United States Patent [19]
Vellender

[11] 3,986,266
[45] Oct. 19, 1976

[54] DENTAL MIRRORS

[76] Inventor: Bernard Francis Vellender, 28, The Avenue, Watford, Hertfordshire, England

[22] Filed: June 23, 1975

[21] Appl. No.: 589,722

[30] Foreign Application Priority Data
July 10, 1974 United Kingdom............... 30586/74
Jan. 29, 1975 United Kingdom................. 3887/75

[52] U.S. Cl. ................................................. 32/69
[51] Int. Cl.² ..................... A61C 3/00; A61C 19/00
[58] Field of Search ........................... 128/10; 32/69

[56] References Cited
UNITED STATES PATENTS
3,014,279  12/1961  Fosdel .................................... 32/69
3,164,904  1/1965  Barnes .................................... 32/69
3,849,889  11/1974  Rosander .............................. 32/69

*Primary Examiner*—Robert Peshock
*Attorney, Agent, or Firm*—Pollock, Vande Sande & Priddy

[57] ABSTRACT

A dental mirror comprising a handle with a reflecting mirror mounted at one end, an air jet tube secured to the handle and arranged to direct a flow of air onto the reflecting face of the mirror, and including a water supply tube from which droplets of water are supplied into the air stream from the air jet tube, this water clearing the mirror face of any debris obscuring the dentist's vision.

9 Claims, 5 Drawing Figures

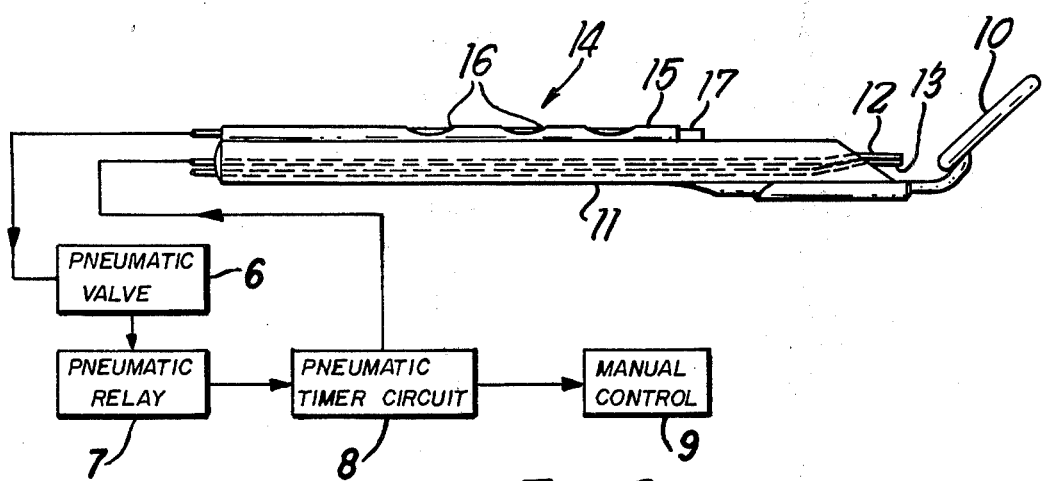
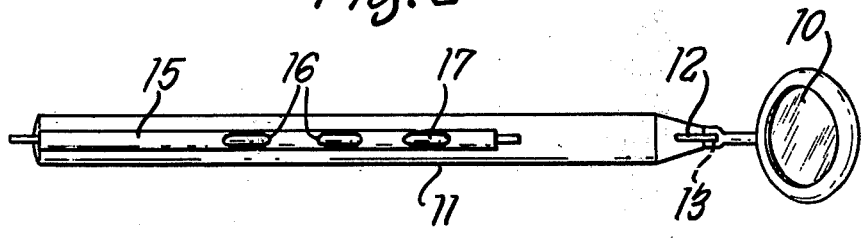

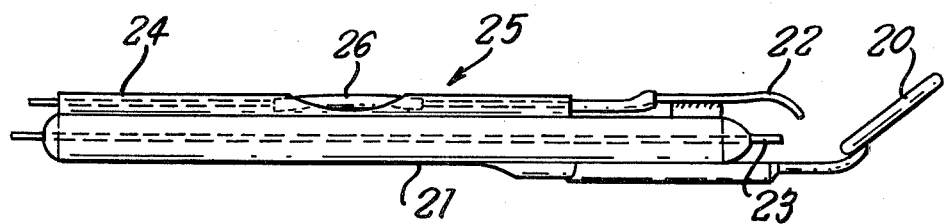
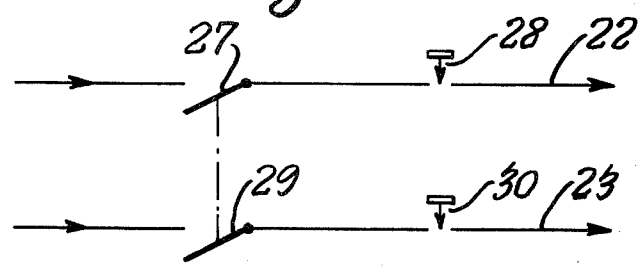
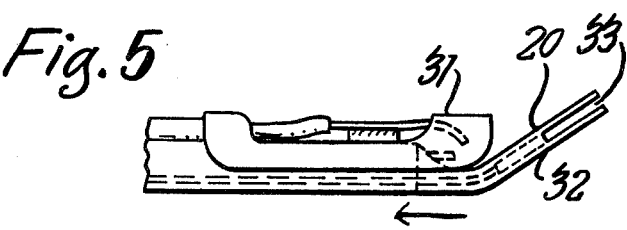

DENTAL MIRRORS

BACKGROUND OF THE INVENTION

The present invention relates to an improved dental mirror.

More particularly it relates to a dental mirror which is provided with a water spray arrangement to clear the reflecting face of the mirror of any saliva or dental debris arising from the dental operation.

During a dental operation, the dentist uses a mirror to check that he is drilling in the right spot and also to check the progress of his work. Debris from the drill and also saliva inside the patient's mouth fall on the mirror during the drilling operation and quickly obscure the dentist's view and hitherto it has been necessary for the dentist continually to stop drilling and withdraw the mirror to wipe it clean. This is naturally disadvantageous and also prolongs the dental operation.

SUMMARY OF THE INVENTION

The mirror according to the present invention allows the dentist to clean the mirror face either continually or whenever necessary without stopping work or withdrawing it from the patient's mouth.

According to the present invention, there is provided a dental mirror comprising a handle with a reflecting mirror mounted at one end thereof, an air jet tube secured to said handle and arranged to direct a flow of air onto the reflecting face of the mirror, and wherein a water supply tube is provided from which droplets of water are supplied into the air stream from said air jet tube.

Preferably means are provided to control the flow of water from said water supply tube.

BRIEF DESCRIPTION OF THE DRAWINGS

Preferred embodiments of the present invention will now be described with reference to the accompanying drawings in which:

FIG. 1 is a side view of a first embodiment of a dental mirror according to the invention, FIG. 2 is a top view of the mirror shown in FIG. 1, FIG. 3 is a side view of a second embodiment of a dental mirror according to the invention, FIG. 4 is a diagrammatic view of a water and air flow control system for use with the mirror shown in FIG. 3, FIG. 5 is a side view of a further example of a dental mirror according to the invention.

DETAILED DESCRIPTION OF THE PREFERRED EMBODIMENT

As shown in FIGS. 1 and 2, a mirror 10 is mounted on a handle 11, the plane of the mirror being at an angle of about 30° – 45° to the axis of the handle. A water spray tube 12 and an air spray tube 13 are mounted in the handle 11 and the tips of the two tubes are directed towards the reflecting face of the mirror 10.

As can be seen, the water tube 12 is positioned above the air tube 13, and the tip of the tube 12 is level with the tip of the tube 13, and the lower edge of the tip of the tube 12 is in contact with the tube 13. The diameter of the tubes 12 and 13 is not critical but as an example of the bore of the water tube 12 is approximately 0.02 cms in diameter and that of the air tube approximately 0.1 cms. The tip of the air tube 13 is approximately ¼ inch away from the mirror 10.

Air under pressure is fed through the tube 13. Water under pressure is fed through the tube 12 and is sucked smoothly away by the stream of air flowing from the tube 13. At the tip of the air tube 13, each drop of water is atomised into a very fine continuous spray which is carried along in the air stream and impinges on the lower edge of the face of the mirror 10. The fine spray spreads over the surface of the mirror to form a very thin continuous film and has sufficient momentum to travel across to the far edge of the mirror thus providing a thin film of water maintained across the mirror surface.

In order not to obscure the dentist's vision, the water emerges from the tube 12 in the form of a series of brief pulses, rather than as a continuous stream. The air flow from the tube 13 is continuous and acts to clear the majority of the debris from the face of the mirror 10 and to ensure that it remains dry. The brief pulses of water from the tube 12 are effective to completely clear the face of the mirror which is subsequently quickly dried by the air stream from the tube 13.

The length and frequency of the water pulses can be determined by a control arrangement to be described.

The disturbance of the dentist's vision when the water pulse occurs is minimal being little more than a brief blink.

An air bleed tube 14 is secured to the outside of the handle 11 and consists of an outer metal sleeve 15 formed with a series of scalloped cut-out portions 16. A soft plastic tube 17 passes down inside the sleeve 15 and is open at its front end to form an air bleed. Pressure of the thumb or finger at one of the cutouts 16 compresses the tube 17 to occlude the air bleed and so operate a pneumatic valve 6.

This valve triggers a pneumatic relay 7 which brings into action a pneumatic timer circuit 8 which controls the frequency and length of the water pulses through the tube 12. A manual control 9 is available to enable the pulse frequency and length to be varied to suit the prevailing condition.

The control of the water pulses can be carried out by any suitable combination of pneumatic, electric or fluidic valves.

On occluding the air bleed tube 17 a second time, the relay switches off the timer and the flow of water pulses ceases, leaving only the continuous air flow. This allows the dentist to carry out a close inspection of his work, after completing a drilling operation for example.

As an alternative, an arrangement can be utilized in which an individual pulse of water can be obtained whenever the air bleed tube is occluded or a continuous regular stream of water can be obtained for as long as the air bleed is occluded. As soon as the finger is removed from the air bleed tube the water flow ceases and a clean dry mirror is obtained.

The use of only short pulses of water means that only very small quantities of water are introduced into the mouth which can readily be removed by a conventional suction tube.

As an alternative to the pipes 12 and 13 being arranged inside the handle 11, these pipes, together with the air bleed tube 14, can be formed and sold as a separate unit which can be attached to the handle of an existing mirror.

As a further alternative, the pipe 12 can be supported inside the pipe 13, such that the air jet coming from the pipe 13 forms an annulus surrounding the water spray from the pipe 12.

As in the embodiment shown in FIGS. 1 and 2, in the second embodiment shown in FIGS. 3 and 4 a mirror 20 is mounted on a handle 21. A water supply tube 22 and an air jet tube 23 are mounted on the handle 21 and the tip of the tube 23 is directed towards the reflecting face of the mirror 20.

As can be seen, in this second embodiment the water tube 22 is positioned above the air tube 23, and the tip of the tube 22 extends in front of the tip of the tube 23.

Air under pressure is fed through the tube 23. Water under low pressure is fed through the tube 22 and issues from the end of the tube 22 in the form of drops which are sucked one by one from the nozzle by the stream of air flowing from the tube 23. Each drop of water is atomised into a very fine continuous spray which is carried along in the air stream and impinges on the lower edge of the face of the mirror 20. The fine spray spreads over the surface of the mirror to form a very thin continuous film and has sufficient momentum to travel across to the far edge of the mirror thus providing a thin film of water across the mirror surface.

In order not to obscure the dentist's vision, the water emerges from the tube 22 in the form of a series of drops rather than as a continuous stream. The air flow from the tube 23 is continuous and acts to clear the majority of the debris from the face of the mirror 20 and to ensure that it remains dry. The brief drops of water from the tube 22 are effective to completely clear the face of the mirror which is subsequently quickly dried by the air stream from the tube 23.

The water supply tube 22 is secured to the outside of the handle 21 and consists of an outer metal sleeve 24 formed with a series of scalloped cut-out portions 25. A soft plastic tube 26 passes down inside the sleeve 24 and is connected at its front end to the tube 22, and at its rear end to a water supply. Pressure of the thumb or finger at one of the cut-outs 25 compresses the tube 26 to cut-off the water supply. Alternatively a lever operated valve may be fitted.

As shown in FIG. 4, a suck-back on/off valve 27 and a flow rate control needle valve 28 are included in the supply pipe to the pipe 22. The valve 27 is operatively linked to an on/off valve 29 in the compressed air supply line connected to the tube 23 such that both air and water supply can be shut off at the same time when necessary. An air regulator valve 30 is also included in the air supply line in order that the air flow rate can be accurately controlled.

The use of only small droplets of water means that only very small quantities of water are introduced into the mouth which can readily be removed by a conventional suction tube.

The tip of the water tube 22 is preferably about 5 mm in front of the tip of the air tube 23 and about the same distance above it. In this way the water from the tube 22 issues as individual drops which fall into the air stream from the tube 23 and are quickly atomised into a fine spray.

As a modification of the arrangement just described, some form of pulsator, such as a pump or a water hammer device, can be provided to ensure that the droplets of water from the tube 23 are of substantially uniform size and that they issue at regular intervals.

FIG. 5 shows a perforated guard 31 which is positioned around the nozzle ends of the tubes 22 and 23 to prevent the lips of the patient's mouth into which the mirror is inserted from touching the tube 22 and interfering with the water flow.

The air and water spray system of the present invention can be used in conjunction with the combined mirror and suction device described in my British Pat. Specification No. 1255719.

FIG. 5 also illustrates the use of such a suction system in which the mirror 20 is mounted on top of a housing 32 which is sealed to the rim of the mirror but is open at the front end 33. The interior of this housing 32 is connected to a suction tube (not shown) which passes down inside the handle 21. Any excess water or saliva in the mouth of the patient is sucked through the opening at 33 and away through the suction tube, as indicated by the arrow.

In a simplified form of the mirror according to the invention the provision of some form of finger operated valve to stop the flow of water droplets from the tubes 17 or 22, can be omitted. All that would be provided in this case would be a main on/off valve in the water supply and the supply of water droplets to the mirror face would then be continuous.

I claim:
1. A dental mirror of the type having a handle with a reflecting mirror mounted at one end thereof comprising:
    first means for directing a continuous flow of air across the reflecting surface of the mirror,
    and second means for discharging water a drop at a time into the air flow provided by said first-named means to be atomized by the air flow and impinge also upon said reflecting surface.
2. A dental mirror as claimed in claim 1, wherein control means are provided to control the flow of water from a water supply tube to said second means.
3. A dental mirror as claimed in claim 2, wherein said control means includes a first valve for controlling the rate of flow of water through said water supply tube and a second valve which is operable to cut-off the flow of water through said tube.
4. A dental mirror as claimed in claim 3, wherein said second valve is pneumatically operated and controllable by way of an air bleed which when occluded causes said second valve to change from its open to its closed state or vice versa.
5. A dental mirror as claimed in claim 3, wherein said second valve is in the form of a deformable elastic portion of said water supply tube which can be manually deformed to cut-off the supply of water along said supply tube.
6. A dental mirror as claimed in claim 1, wherein a protective guard is positioned around the open ends of said air jet tube and water supply tube.
7. A dental mirror as claimed in claim 1, wherein the open end of said water supply tube is positioned in front of and above the open end of said air jet tube, with respect to the reflecting face of said mirror.
8. A dental mirror as claimed in claim 1, wherein said mirror is combined with a suction means whereby any excess liquid adjacent said mirror can be removed.
9. A dental mirror as claimed in claim 8, wherein said suction means is in the form of a cavity at the rear of the reflecting face of said mirror, which cavity is formed with one or more apertures whereby liquid can enter said cavity and be removed by way of a suction pipe communicating with said cavity.

* * * * *